(12) United States Patent
Clements (10) Patent No.: US 9,427,350 B1
(45) Date of Patent: Aug. 30, 2016

(54) ANKLE SUPPORT WITH CABLE REEL

(71) Applicant: DeRoyal Industries, Inc., Powell, TN (US)

(72) Inventor: Karen M. Clements, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 440 days.

(21) Appl. No.: 13/721,166

(22) Filed: Dec. 20, 2012

(51) Int. Cl.
*A61F 5/01* (2006.01)

(52) U.S. Cl.
CPC ............... *A61F 5/0127* (2013.01); *A61F 5/01* (2013.01)

(58) Field of Classification Search
CPC .. A61F 5/0111; A61F 5/0113; A61F 5/0127; A61F 13/066; A43C 11/165
See application file for complete search history.

(56) References Cited

U.S. PATENT DOCUMENTS

| | | |
|---|---|---|
| 1,465,970 A | 8/1923 | Cleveland et al. |
| 3,699,959 A | 10/1972 | Garrahan et al. |
| 4,392,487 A | 7/1983 | Selner et al. |
| 4,844,094 A | 7/1989 | Grim |
| 4,869,267 A | 9/1989 | Grim et al. |
| 4,948,092 A | 8/1990 | Kasper et al. |
| 4,962,768 A | 10/1990 | Stromgren et al. |
| 4,964,402 A | 10/1990 | Grim et al. |
| 5,026,339 A | 6/1991 | Kasper |
| 5,027,801 A | 7/1991 | Grim |
| 5,067,486 A | 11/1991 | Hely |
| 5,088,478 A | 2/1992 | Grim |
| 5,209,722 A | 5/1993 | Miklaus et al. |
| 5,348,530 A | 9/1994 | Grim et al. |
| 5,445,602 A | 8/1995 | Grim et al. |
| 5,620,413 A | 4/1997 | Olson |
| 5,676,641 A | 10/1997 | Arensdorf et al. |
| 5,716,335 A | 2/1998 | Iglesias et al. |
| 5,795,316 A | 8/1998 | Gaylord |
| 5,951,504 A | 9/1999 | Iglesias et al. |
| 6,053,884 A | 4/2000 | Peters |
| 6,117,098 A | 9/2000 | Weber et al. |
| 6,454,733 B1 | 9/2002 | Krusenklaus |
| 6,460,275 B1 | 10/2002 | Bennett et al. |
| 6,524,266 B1 | 2/2003 | Peters |
| 6,602,215 B1 | 8/2003 | Richie, Jr. |
| 6,641,550 B1 | 11/2003 | Johnson |
| 6,749,578 B2 | 6/2004 | Peters |
| 6,858,017 B2 | 2/2005 | Peters |
| D552,744 S | 10/2007 | Verkade et al. |
| 7,828,758 B2 | 11/2010 | Clements et al. |
| 8,100,845 B2 | 1/2012 | Clements et al. |
| 8,317,735 B2 | 11/2012 | Clements et al. |
| 2004/0019309 A1* | 1/2004 | Nelson ............... A61F 5/0111 602/65 |
| 2009/0247922 A1* | 10/2009 | Clements ............ A61F 5/0127 602/27 |
| 2012/0029404 A1* | 2/2012 | Weaver, II ........... A61F 5/0111 602/27 |

* cited by examiner

*Primary Examiner* — Kari Petrik (74) *Attorney, Agent, or Firm* — Luedeka Neely Group, PC (57) ABSTRACT

An ankle support for controlling motion of an ankle joint of a user, the support including a body portion configured to be positioned on a lower leg of the user adjacent the foot; a reel connected to the support; one or more tensionable members windable onto the reel and extending from the reel; strap portions wrapped about a portion of the foot when the support is installed on the user, the strap portions being connected to the tensionable members. The strap portions are tensioned and secured in the tensioned state to limit movement of the foot by winding the tensionable members onto the reel.

7 Claims, 14 Drawing Sheets

ANKLE SUPPORT WITH CABLE REEL

FIELD

This disclosure relates to the field of ankle supports. More particularly, this disclosure relates to an ankle support wearable alone or inside a shoe which is configured to have improved fit and adjustability.

BACKGROUND

Ankle supports are often worn as treatment for an ankle sprain or to prevent an ankle sprain. Desirably, an ankle support is lightweight, compact so as to be able to be worn inside a shoe, supports the ankle and foot to limit inversion and eversion, but does not otherwise limit the flexion motions associated with the toe-up and toe-down motions of a normal gait. Prior devices designed to meet these objectives desire improvement in fit and adjustability.

SUMMARY

The above and other needs are met by a support for controlling motion of a foot of a user. In one aspect, the support includes a body portion configured to be positioned on a lower leg of the user adjacent the foot; a reel connected to the support; one or more tensionable members windable onto the reel and extending from the reel; and strap portions wrapped about a portion of the foot when the support is installed on the user. The strap portions are connected to the tensionable members, and the strap portions are tensioned and secured in the tensioned state to limit movement of the foot by winding the tensionable members onto the reel.

In another aspect, there is provided an ankle support for limiting movement of the ankle joint and foot of the user. The support includes a body portion configured to be positioned on a lower leg of the user adjacent the ankle joint; a reel connected to the ankle support; one or more tensionable members windable onto the reel and extending from the reel; and a control strap system for limiting movement of the ankle joint and foot of the user.

The control strap system includes one or more straps configured to wrap around a portion of the foot to provide strap portions that extend in opposite directions over an upper portion of the foot when the support is installed onto the ankle joint. The strap portions are connected to the tensionable members so that the tensionable members secure the body portion about the lower leg of the user and the straps limit movement of the foot when the straps are tensioned and secured in the tensioned state by winding the tensionable members onto the reel.

In a further aspect, there is provided an ankle support for limiting movement of the ankle joint and foot of the user. The support includes a body portion configured to be positioned on a lower leg of the user adjacent the ankle joint; a reel connected to the ankle support; one or more tensionable members windable onto the reel and extending from the reel; a strap system for limiting movement of the ankle joint and foot of the user; a heel plate hingedly coupled to the body portion and configured for supporting the heel of the user; and a heel liner releasably secured to the heel plate, with the liner including an anchor sleeve providing a passage for passage of the straps underneath the foot of the user.

The control strap system includes a pair of straps configured to engage a heel of the foot of the user and wrap around a portion of the foot and extend in opposite directions over an upper portion of the foot when the support is installed onto the ankle joint. The straps are connected to the tensionable members and the straps are tensioned and secured in the tensioned state by winding the tensionable members onto the reel to limit movement of the foot.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

The disclosure relates to an ankle support 10 that is lightweight and compact so as to be wearable inside a shoe if desired. The support 10 is useful for instabilities of the ankle, including treatment of ankle sprains and overuse issues such as posterior tibial and peroneal tendonitis.

Features of the support 10 include a heel strap system that holds the calcaneous under the talus of the foot to control subtalar inversion and talar rotation, rigid medial and lateral uprights to help prevent abnormal eversion and inversion, a low profile configuration that enables the support to fit within a shoe, and a tensionable cable for tightening the heel strap system and securing the support 10 for ease of use and ease of adjustment. It has been observed that supports according to the disclosure support the ankle and foot to limit inversion and eversion, but do not otherwise limit the flexion motions associated with the toe-up and toe-down motions of a normal gait.

With reference to the drawings, the support 10 includes a generally U-shaped flexible body 12, a tongue 14, pair of rigid uprights 16 and 18, a rigid generally U-shaped heel plate 20 pivotally attached to the uprights, a heel liner 22, a control strap system 24, and a cable reel system 26.

The body 12 is preferably made of a flexible and lightweight nylon fabric material. The body 12 is configured to substantially surround the lower leg of the user and conform thereto when tensioned using the cable reel system 26. The body 12 may be made of a padded nylon material and includes a pair of sleeves 12a and 12b on opposite sides thereof which are configured for securably receiving the uprights 16 and 18 and maintaining the uprights 16 and 18 on opposite sides of the leg of the user.

The tongue 14 is made of a soft flexible material and the tongue 14 may be provided to span the gap occasioned by the U-shape of the body 12 at the front of the body 12. The tongue 14 is free relative to the body 12, but, is preferably yieldably connected to a rear portion of the body 12 as by elastic members 30, such as elastic straps, that extend from opposite sides of the exterior of the body 12 to portions of the tongue 14 proximate the sides of the tongue 14. When the support 10 is positioned on the foot of the user, the elastic members 30 are located on opposite sides of the foot of the user and urge the tongue 14 toward the body 12.

The uprights 16 and 18 are each made of a lightweight and substantially rigid material, such as aluminum or plastic having sufficient rigidity so as to substantially avoid bending during use. Preferred materials include glass-filled nylon polypropylene. The uprights 16 and 18 are configured to be received within the sleeves 12a and 12b to lie on opposite sides of the leg of the user, and extend up the sides of the shin or lower leg from a location adjacent the lowermost portions of the tibia and the fibula.

The heel plate 20 is preferably of one-piece construction and made of a thin, lightweight and substantially rigid material, such as aluminum or plastic having sufficient rigidity so as to substantially avoid bending during use. If desired, the plate 20 may be heat moldable or the like to enable it to be customized to the foot of the user. The plate 20 is sufficiently thin to avoid interference with fit when installing within a shoe. The plate 20 includes a central portion 40 that underlies the heel of the user and extensions 42 and 44 that extend upwardly from opposite sides of the central portion.

The extensions 42 and 44 pivotally connect to the uprights 16 and 18 as by hinges 46 provided as by aligned apertures and pins. The hinges 46 do not permit side to side motion of the lower ends of the uprights, such that the rigidity of the uprights 16 and 18 and the rigidity of the heel plate 20 limit side to side motion of the assembled uprights 16 and 18 and the heel plate 20.

The heel liner 22 is configured to overlie the central portion of the heel plate 20 and is made of a thin, flexible material to pad and wick moisture from the foot. The heel liner 22 is releasably secured to the plate 20 as by mating pieces of hook and loop material 48. The heel liner 22 is preferably cup-shaped to seat the heel of the foot. An anchor sleeve 50 is located on the upper surface of the heel liner. The anchor sleeve 50 is provided, for example, by a strip of fabric material longitudinally aligned with the length of the heel liner 22, with the ends thereof secured to the liner and the remainder unsecured so as to provide a through passage. As described in more detail below, straps associated with the strap system 24 are passed through the passage of the anchor sleeve 50 so as to anchor them in location relative to the calcaneous of the foot, but permit them to be tensioned.

The control strap system 24 may include a pair of straps 60 and 62 having anchored ends 60a and 62a, respectively, and opposite free ends 60b and 62b. As will be appreciated, the straps 60 and 62 may be provided as by a single strap instead of two separate straps, the single strap having ends that extend to provide the opposite free ends 60b and 62b. The straps 60 and 62 are made of a flexible and preferably slightly elastic material. The strap system 24 is configured to substantially maintain the orientations of the straps 60 and 62 whether the straps 60 and 62 are tensioned or untensioned. This simplifies use of the support 10 in that the user need only untension the straps 60 and 62 using the cable reel system 26 to install the support, and thereafter tension the straps 60 and 62 using the cable reel system 26 to secure the support 10 onto the foot and lower leg of the user, with the straps 60 and 62 limiting movement of the foot.

The anchored ends 60a and 62a of the straps 60 and 62 are secured on opposite sides of the interior of the body 12, as by stitches or the like, so as to be located on opposite sides of the ankle joint. The straps 60 and 62 are overlapped at a location near the anchored ends 60a and 62a so as to provide a calcaneous receiver 64 that can be positioned around the back of the calcaneous and fittingly receive the calcaneous. Stitches or the like are preferably provided at the location of the receiver 64 to secure the straps 60 and 62 together at this location.

The free ends 60b and 62b of the straps 60 and 62 are threaded from opposite sides through the passage provided by the anchor sleeve 50 on the heel liner 22 and are crossed over one another. When the heel is placed on the heel liner 22, the straps 60 and 62 extend from under the foot and cross over the foot so that the straps 60 and 62 are wrapped around the talonavicular joint of the foot of the user. The free ends 60b and 62b of the straps 60 and 62 extend upwardly away from opposite sides of the foot and are connected to the cable reel system 26. The cable reel system 26 enables the straps 60 and 62 to be tensioned and secured in the tensioned state to limit movement of the foot.

A strap guide 66 may be provided to guide the straps 60 and 62 above the foot to maintain the straps 60 and 62 in their desired overlapped positions when the straps 60 and 62 are in an untensioned state. The guide 66 may be provided as by a strip of material over which the straps 60 and 62 pass and having an elastic strap spanning over the strip of material to overlie the straps 60 and 62, with the elastic strap extending to and secured to an upper portion of the tongue 14.

The cable reel system 26 is operated to untension the straps 60 and 62 to enable the support 10 to be installed on the foot and lower leg of the user. Once the support 10 is installed, the cable reel system 26 is operated to tension the straps 60 and 62 about the foot and heel and to tighten the support 10 about the leg of the user. The cable reel system 26 includes a cable reel 70 having a tensionable member such as a cable 72 extending from the reel 70, and cable guides 74 affixed to portions of the support 10. The cable 72 may be one or more cables.

The reel 70 is a spring-loaded rotating spool that winds or unwinds the cable 72 to either tension or untension the cable 72. Suitable devices to use for the reel 70 are cable reel devices available under the name BOA from Boa Technology, Inc. of Denver, Colo., and described in U.S. Pat. Nos. 7,954,204 and 7,992,261, incorporated by reference in their entireties. The reel 70 is fixedly mounted to the support 10. For example, as shown, the reel 70 is mounted to an upper rear portion of the body 12.

The cable 72 may be a low friction nylon coated, stainless steel cable or other low friction flexible lacing like material. The guides 74 are located so as to train the cable 72 in a desired manner to achieve tightening of the body 12 about the leg of the user and tensioning of the straps 60 and 62. As shown, the guides 74 are located at various locations on the body 12 and on the tongue 14. The guides 74 may be entirely located on the body 12 if desired. In this regard, the guides 74 are located so as to route the cable 72 so that the cable 72 when tensioned tightens the body 12 about the lower leg of the user and also tensions the straps 60 and 62 and maintain such tension with the receiver 64 engaging the calcaneous and the tension in the straps 60 and 62 serving to limit movement of the ankle joint and the foot. The free ends 60b and 62b of the straps 60 and 62 may include a sleeve 76 through which the cable 72 passes. The sleeve 76 enables the cable 72 to easily slide therethrough.

Figure 1:
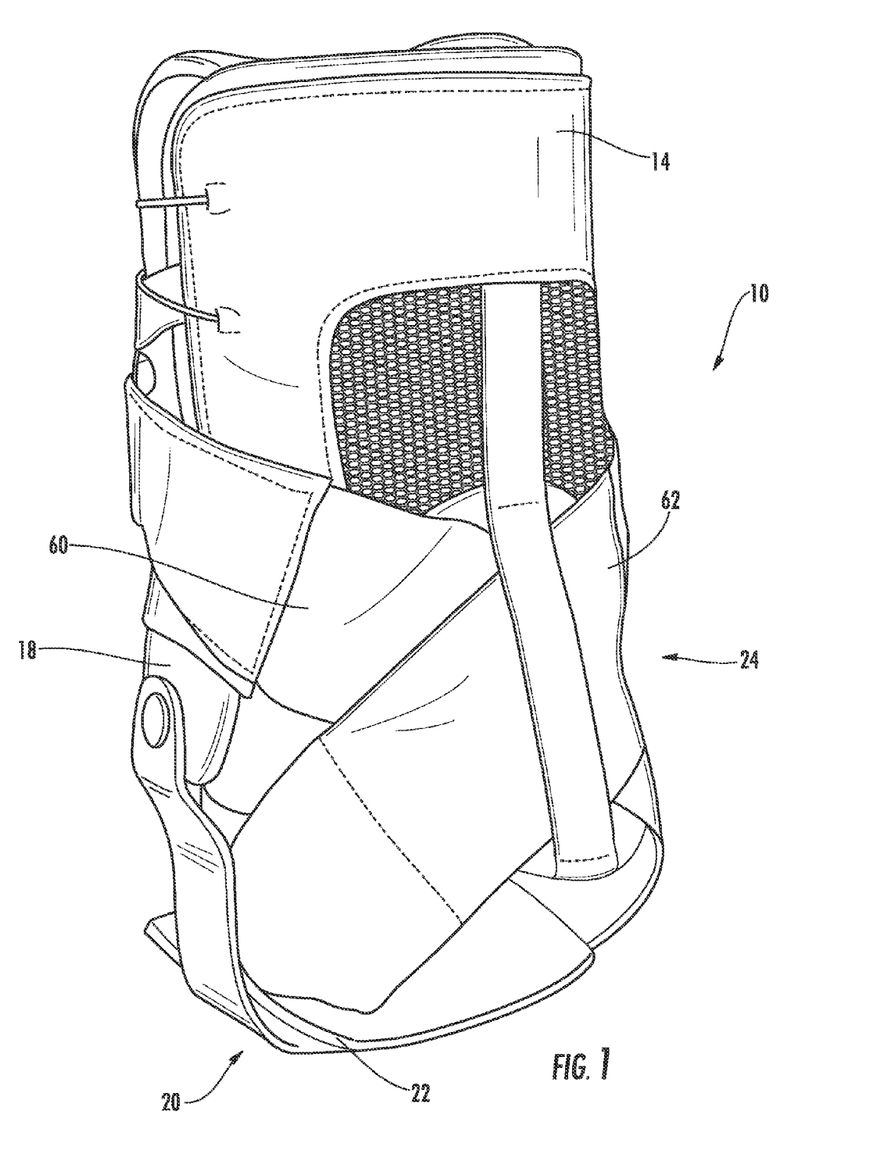
FIG. 1 is a front view of an ankle support according to the disclosure.
Figure 2:
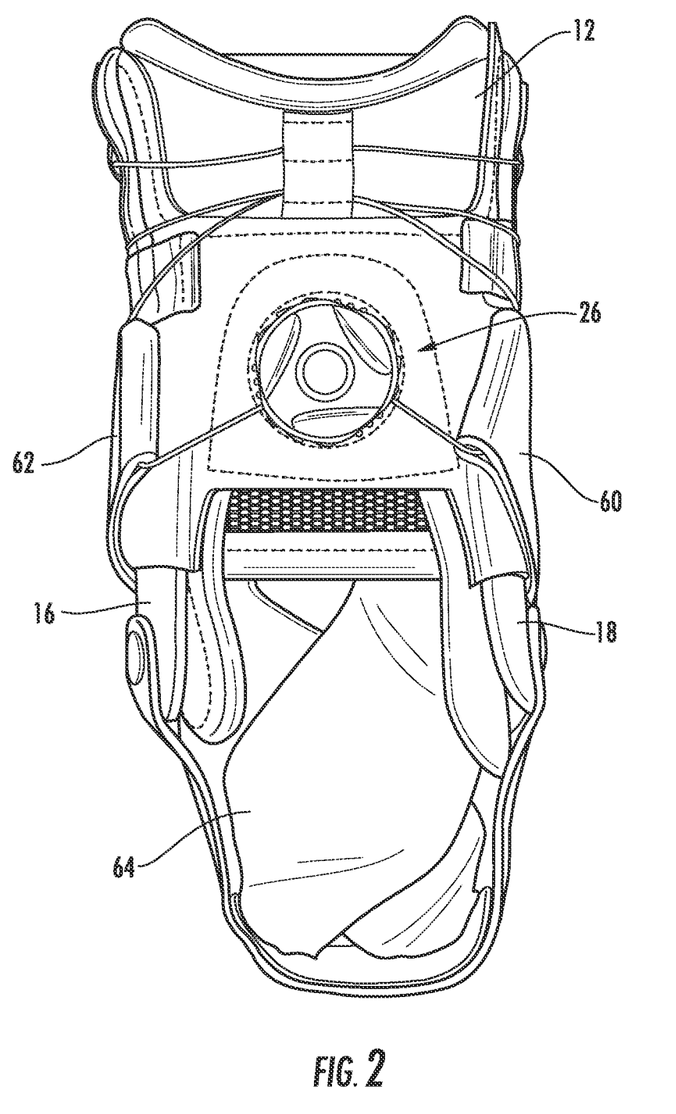
FIG. 2 is a rear view of the ankle support of FIG. 1.
Figure 3:
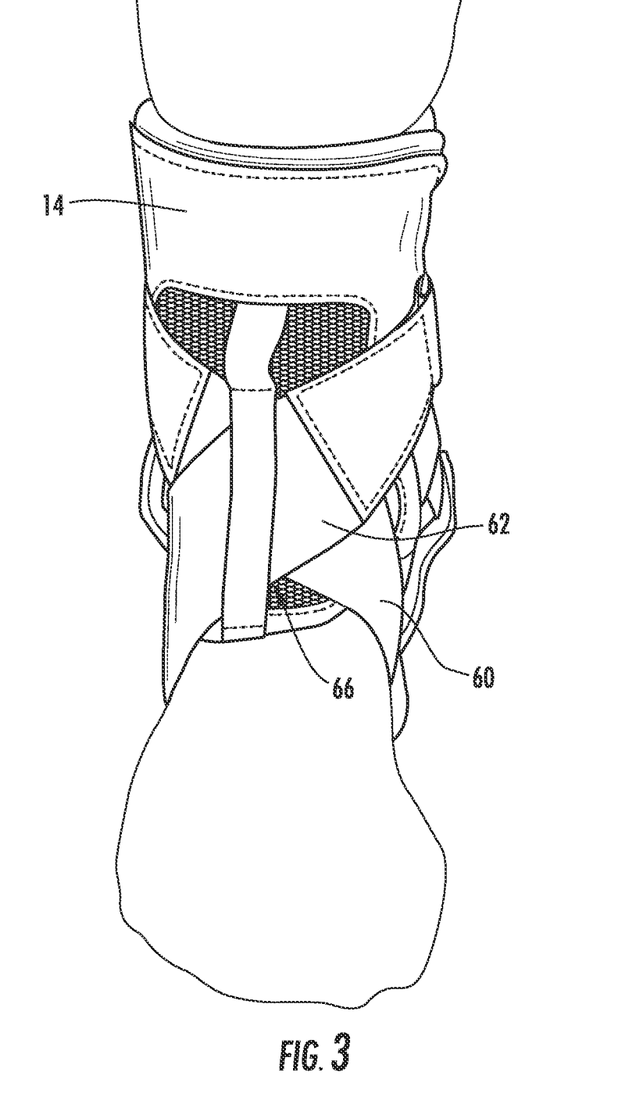
FIG. 3 is a front view showing the ankle support of FIG. 1 installed on an ankle.
Figure 4:
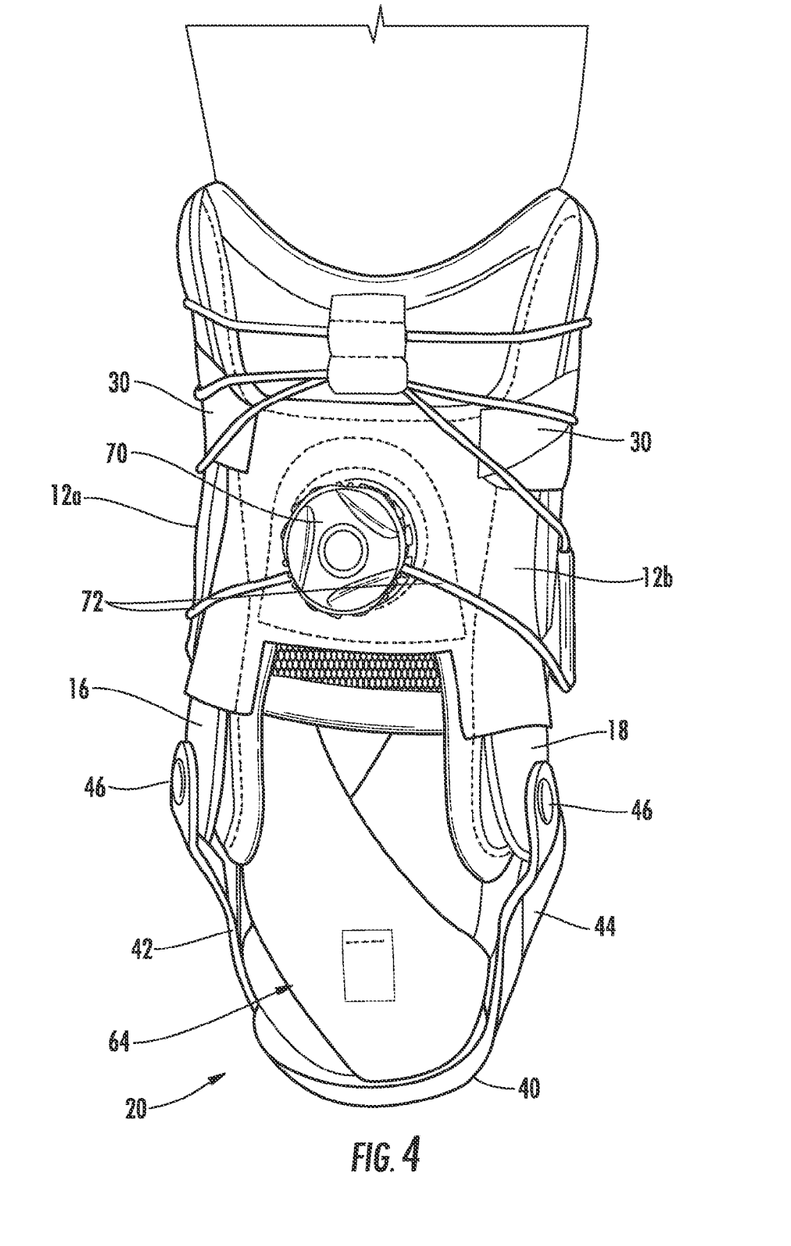
FIG. 4 is a rear view showing the ankle support of FIG. 1 installed on an ankle.
Figure 5:
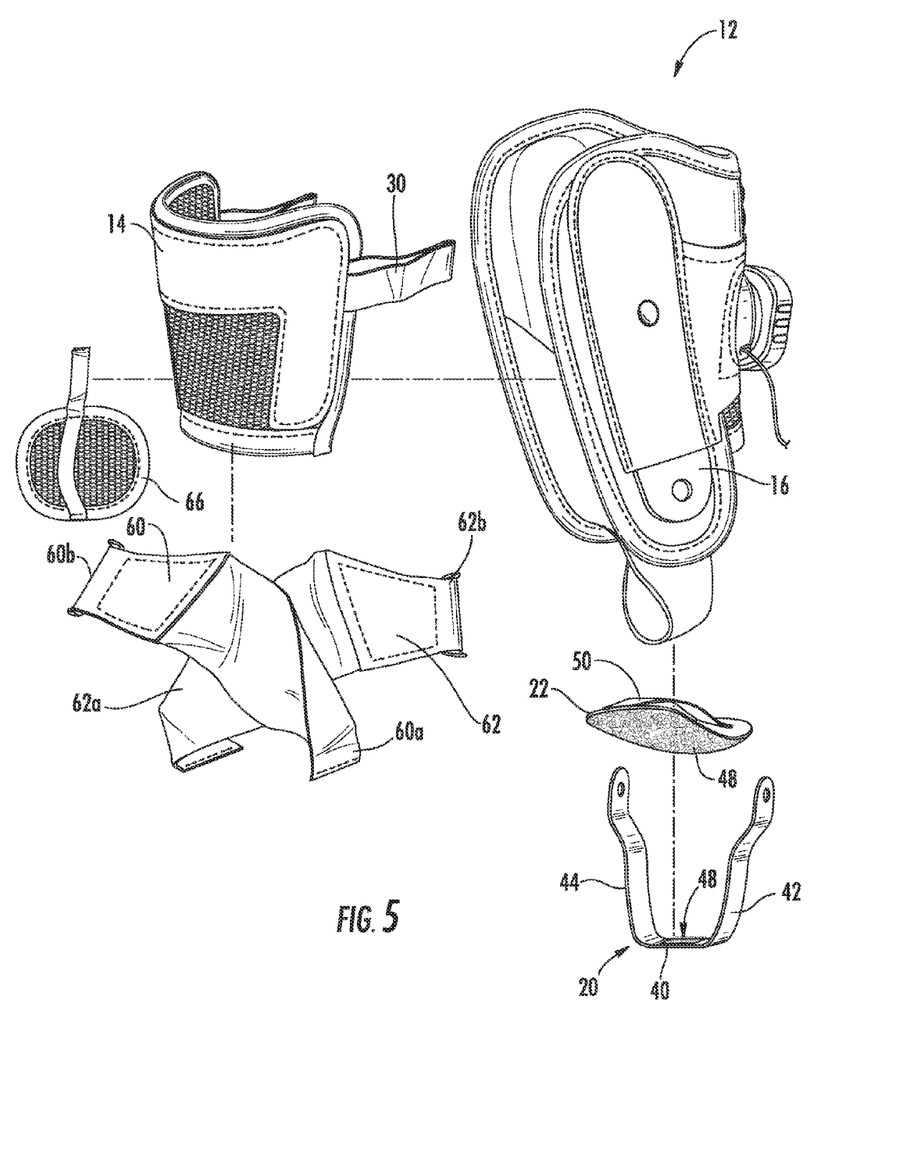
FIG. 5 is an exploded view of the ankle support of FIG. 1.
Figure 6:
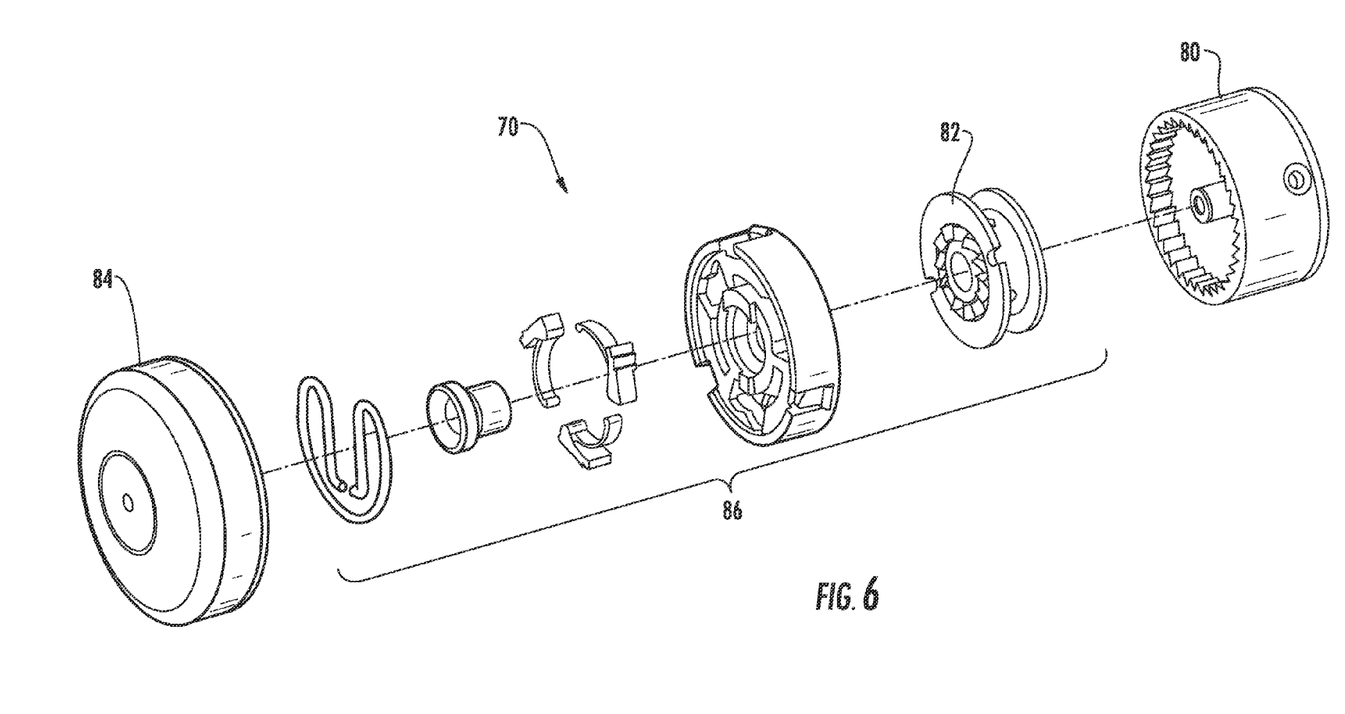
FIG. 6 is an exploded perspective view of a cable reel component of the support of FIG. 1.
Figure 7:
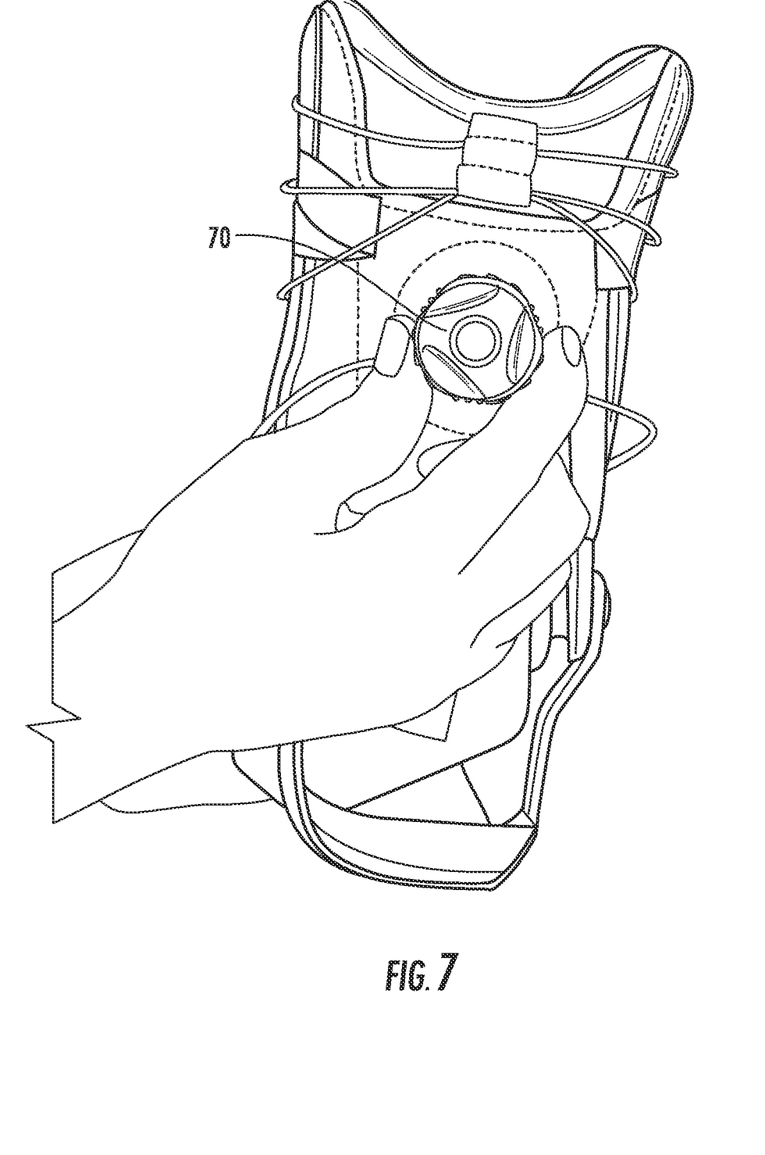
FIGS. 7-14 depict exemplary installation of the ankle support of FIG. 1 onto an ankle.
Figure 8:
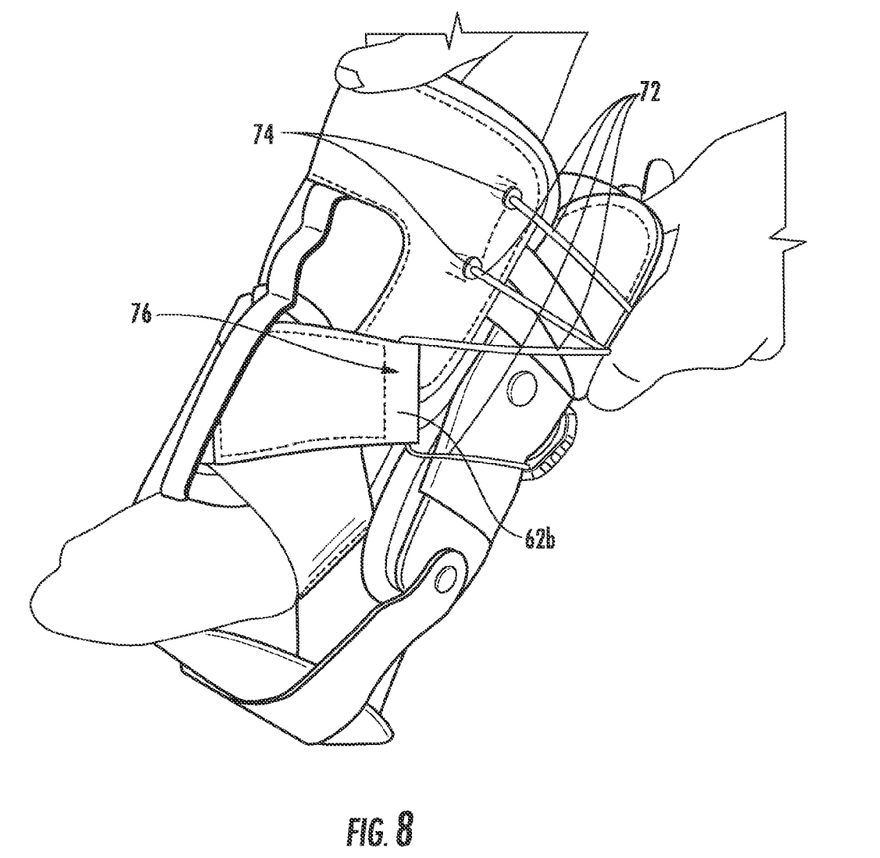
Figure 9:
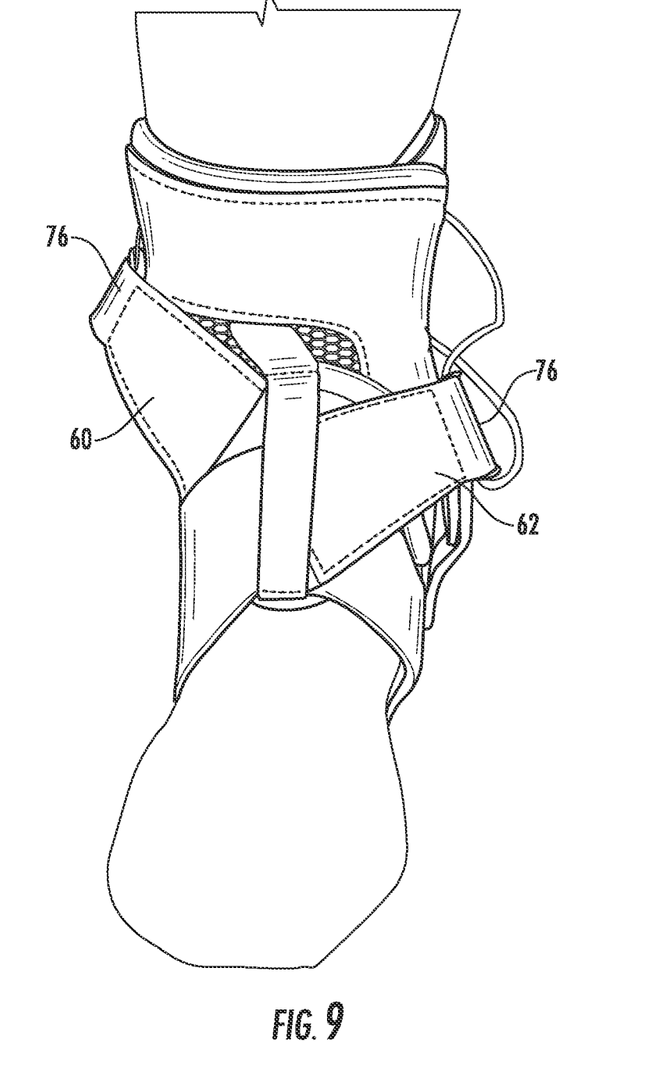
Figure 10:
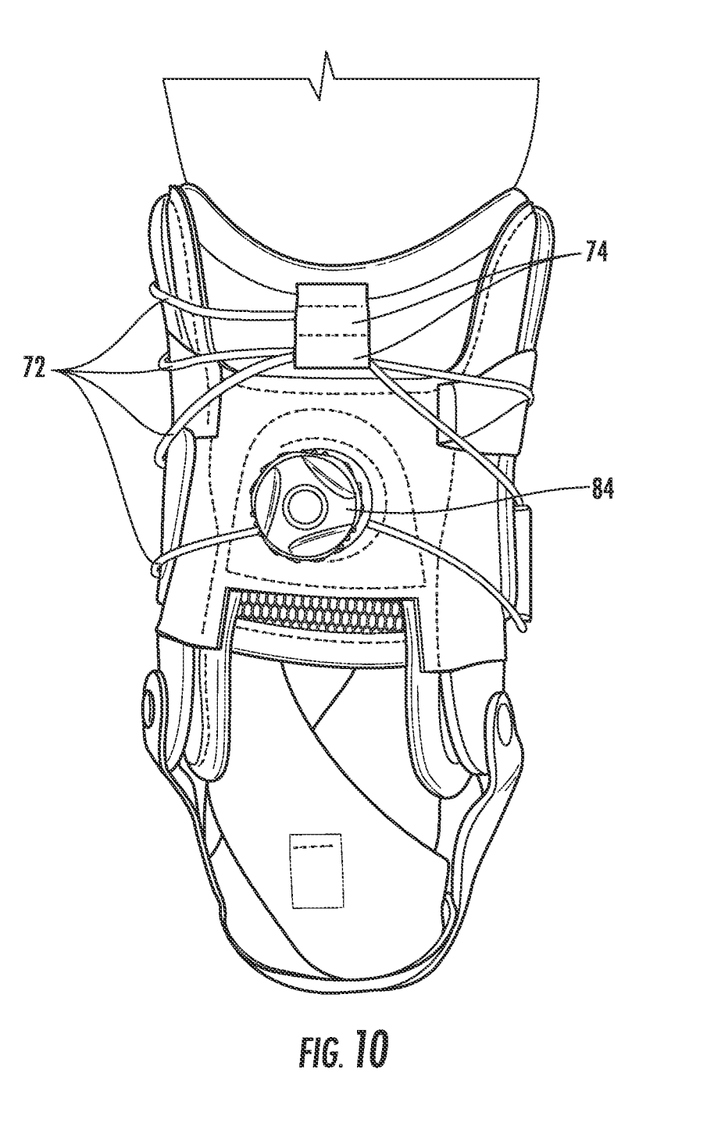
Figure 11:
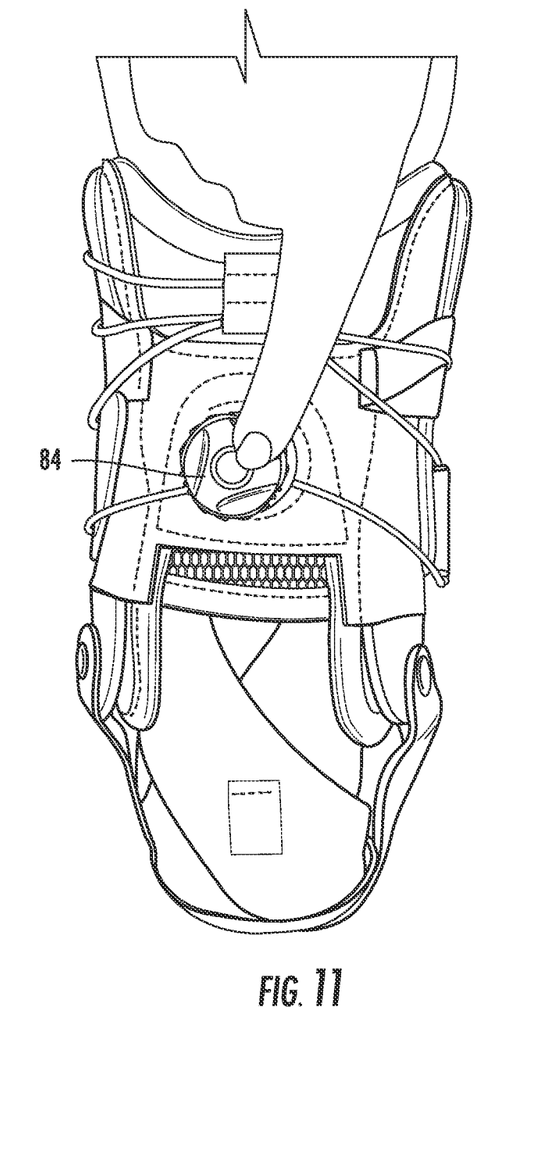
Figure 12:
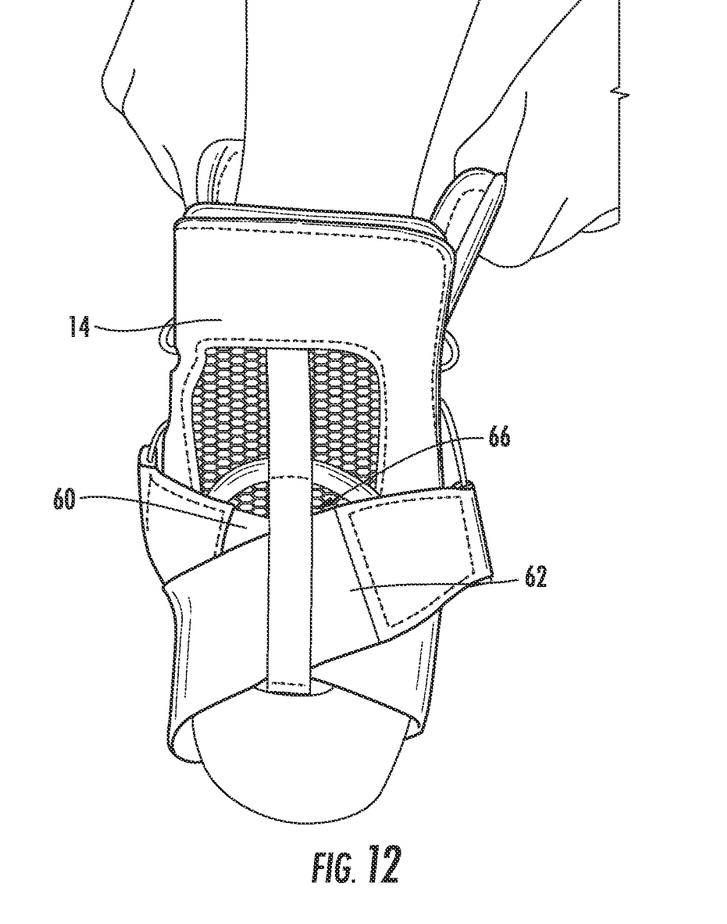

With reference to FIG. 6, the cable reel 70 is a rotating spool that winds or unwinds the cable 72 and, preferably includes a toothed housing 80 configured for receiving the cable 72 and rotationally link the cable 72 to a spool 82 contained within the housing 80. A knob 84 having a spring-loaded assembly 86 cooperates with the housing 80 and the spool 82 for manually winding the cable 72 around the spool 82. The knob 84 and spring-loaded assembly 86 cooperate to engage the spool 82 with the housing 80 to provide a ratchet feature for winding the spool 82 when the knob 84 is turned in one direction to tension the cable 72, and for releasing the spool 82 to untension the cable 72.

With reference to FIGS. 7-12, the support 10 may be installed onto an ankle by initially pull out on the knob 84 to disengage the reel 70 and release the cable 72 and pulling a sufficient amount of the cable 72 free from the spool 82 to assist in easy donning of the support 10 onto the ankle and leg of the user. The foot of the user may then be slid into the support 10 via the top opening of the body 12, with the knob 84 oriented at the back of the support 10 and the foot protruding from the support 10. The foot is preferably positioned in the support 10 at a 90° angle, with the heel or calcaneous as far back in the support 10 as possible so that the heel is received in the receiver 64 and the straps 60 and 62 cup the heel. The knob 84 is then pushed in to engage the reel 70, and the knob 84 is turned clockwise to tighten the cable 72 and tension the straps 60 and 62 and also tighten the body 12 about the leg of the user. The knob 84 may be manipulated to adjust the cable 72 to provide a secure and comfortable fit with the straps 60 and 62 tensioned sufficiently to limit movement of the foot.

Figure 13:
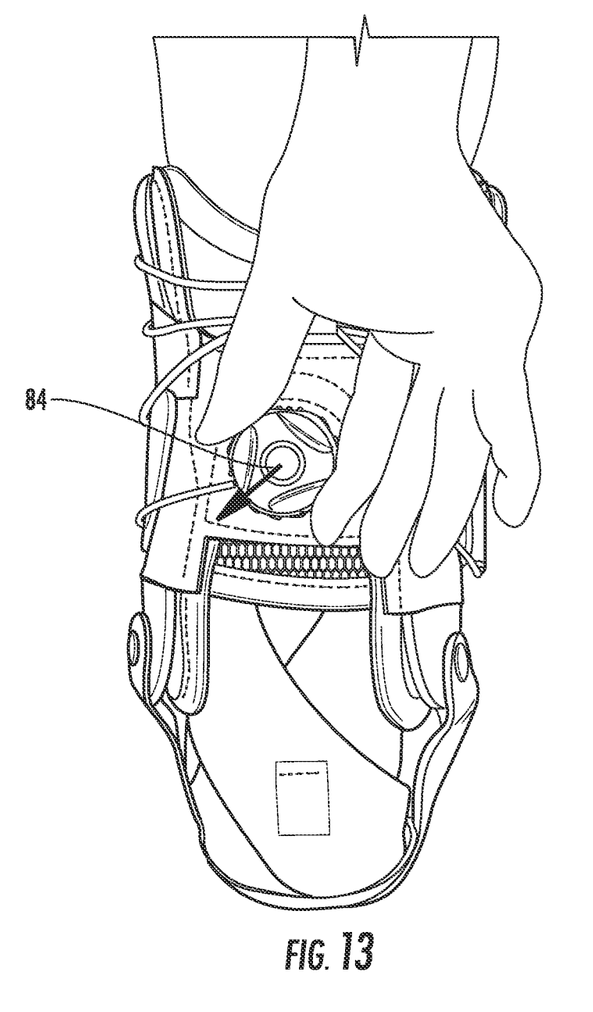
Figure 14:
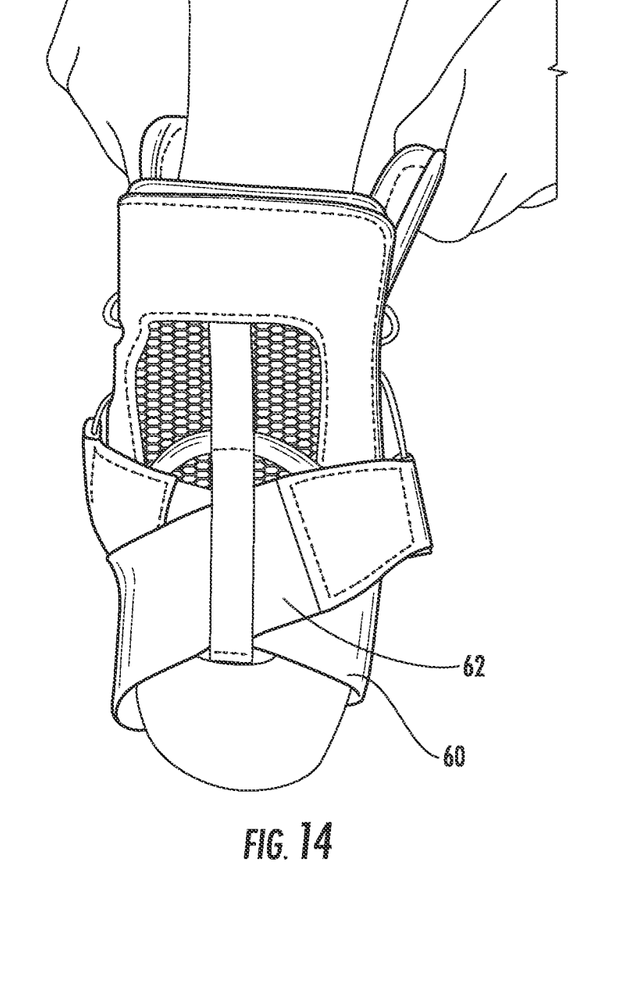

To remove the support 10, and with reference to FIGS. 13 and 14, the knob 84 is pulled out to disengage the reel 70 and release tension from the straps 60 and 62. The foot may then be slid out of top of the support 10.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. An ankle support for limiting movement of an ankle joint and foot of a user, the ankle support comprising:
    a body portion configured to be positioned on a lower leg of the user adjacent the ankle joint;
    a tongue connected to the body portion;
    a heel plate hingedly coupled to the body portion and configured for supporting a heel of the user;
    a reel connected to the body portion;
    one or more tensionable members windable onto the reel and extending from the reel; and
    a control strap system for limiting movement of the ankle joint and foot of the user, the control strap system comprising a strap guide and one or more straps configured to be positionable in a desired orientation in which the one or more straps extend from under the foot and cross over the foot so as to wrap around a portion of the foot to provide distal strap portions that extend in opposite directions over an upper portion of the foot when the ankle support is installed onto the ankle joint, the distal strap portions being connected to the one or more tensionable members so that the one or more tensionable members secure the body portion about the lower leg of the user and the one or more straps limit movement of the foot when the one or more straps are tensioned and secured in a tensioned state by winding the one or more tensionable members onto the reel, the strap guide being located on the tongue and configured to cooperate with the distal strap portions adjacent the upper portion of the foot to maintain the desired orientation of the one or more straps whether the one or more straps are tensioned or untensioned.

2. The ankle support of claim 1, wherein the body portion further includes a pair of rigid uprights located to lie on opposite sides of the lower leg of the user.

3. The ankle support of claim 1, further comprising a heel liner releasably secured to the heel plate, with the heel liner including an anchor sleeve providing a passage for passage of the one or more straps underneath the foot of the user.

4. The ankle support of claim 1, wherein the one or more tensionable members each comprises a cable.

5. The ankle support of claim 1, wherein the tongue is yieldably connected to a rear portion of the body portion by elastic members.

6. The ankle support of claim 1, wherein the reel is mounted on a rear surface of the body portion.

7. An ankle support for limiting movement of an ankle joint and foot of a user, the ankle support comprising:
    a body portion configured to be positioned on a lower leg of the user adjacent the ankle joint;
    a tongue connected to the body portion;
    a reel connected to the body portion;
    one or more tensionable members windable onto the reel and extending from the reel;
    a control strap system for limiting movement of the ankle joint and foot of the user, the control strap system comprising a strap guide and a pair of straps configured to be positionable in a desired orientation in which the pair of straps engage a heel of the foot of the user and wrap around a portion of the foot and extend in opposite directions over an upper portion of the foot when the ankle support is installed onto the ankle joint, the pair of straps being connected to the one or more tensionable members, the strap guide being located on the tongue and configured to cooperate with the pair of straps adjacent the upper portion of the foot to maintain the desired orientation of the pair of straps whether the pair of straps are tensioned or untensioned; a heel plate hingedly coupled to the body portion and configured for supporting the heel of the user; and a heel liner releasably secured to the heel plate, with the heel liner including an anchor sleeve providing a passage for passage of the pair of straps underneath the foot of the user; wherein the pair of straps are tensioned and secured in the tensioned state by winding the one or more tensionable members onto the reel to limit movement of the foot.

* * * * *